US008821455B2

(12) United States Patent
Burkholz et al.

(10) Patent No.: US 8,821,455 B2
(45) Date of Patent: Sep. 2, 2014

(54) ANTIMICROBIAL COATING FOR DERMALLY INVASIVE DEVICES

(75) Inventors: Jonathan Karl Burkholz, Salt Lake City, UT (US); Minh Quang Hoang, Sandy, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 12/831,880

(22) Filed: Jul. 7, 2010

(65) Prior Publication Data
US 2011/0009831 A1 Jan. 13, 2011

Related U.S. Application Data

(60) Provisional application No. 61/224,168, filed on Jul. 9, 2009.

(51) Int. Cl.
*A61M 25/00* (2006.01)
*A61M 5/32* (2006.01)
*A61L 29/16* (2006.01)
*A61L 29/08* (2006.01)

(52) U.S. Cl.
CPC ............ *A61L 29/085* (2013.01); *A61L 29/16* (2013.01); *A61L 2300/404* (2013.01); *A61L 2300/442* (2013.01)
USPC ...................................................... 604/265

(58) Field of Classification Search
CPC ............ A61L 2300/404; A61L 27/54; A61L 2202/24; A61L 2400/10; A61L 2420/02; A61M 2025/0056; A61M 2025/0057; A61M 25/0111
USPC ................................................... 604/265–269
See application file for complete search history.

(56) References Cited

U.S. PATENT DOCUMENTS

| 3,223,629 | A | | 12/1965 | Loeffler |
| 4,339,336 | A | | 7/1982 | Hammond et al. |
| 4,584,192 | A | | 4/1986 | Dell et al. |
| 4,603,152 | A | * | 7/1986 | Laurin et al. ................. 604/265 |
| 4,629,743 | A | | 12/1986 | Hong |
| 4,629,746 | A | | 12/1986 | Michl et al. |
| 4,642,126 | A | | 2/1987 | Zador et al. |
| 4,676,782 | A | * | 6/1987 | Yamamoto et al. ........... 604/175 |
| 4,677,143 | A | | 6/1987 | Laurin et al. |

(Continued)

FOREIGN PATENT DOCUMENTS

| CN | 1526771 A | 9/2004 |
| CN | 101353545 A | 1/2009 |

(Continued)

OTHER PUBLICATIONS

Gama Healthcare, Clinell Alcoholic 2% Chlorhexidine, http://www.gamahealthcare.com/clinellaca2c.html, pp. 1-3, Nov. 7, 2008.

(Continued)

*Primary Examiner* — Rebecca E Eisenberg
(74) *Attorney, Agent, or Firm* — Jeanne Lukasavage; Craig Metcalf; Kirton McConkie

(57) ABSTRACT

An antimicrobial coating applied to a transdermal surface of a catheter device. An antimicrobial coating applied to catheter device such that when the catheter device is fully inserted, the antimicrobial coating is interposed between the catheter device and the dermal layers of the patient.

21 Claims, 12 Drawing Sheets

(56) References Cited

U.S. PATENT DOCUMENTS

| | | | |
|---|---|---|---|
| 4,716,032 A | 12/1987 | Westfall et al. | |
| 4,798,594 A | 1/1989 | Hillstead | |
| 4,895,566 A | 1/1990 | Lee | |
| 4,915,934 A | 4/1990 | Tomlinson | |
| 4,925,668 A | 5/1990 | Khan et al. | |
| 4,955,890 A * | 9/1990 | Yamamoto et al. | 606/108 |
| 4,985,399 A | 1/1991 | Matsuda et al. | |
| 5,023,082 A | 6/1991 | Friedman et al. | |
| 5,217,493 A | 6/1993 | Raad et al. | |
| 5,366,505 A | 11/1994 | Farber | |
| 5,456,948 A | 10/1995 | Mathisen et al. | |
| 5,512,199 A | 4/1996 | Khan et al. | |
| 5,540,661 A | 7/1996 | Tomisaka et al. | |
| 5,547,662 A | 8/1996 | Khan et al. | |
| 5,616,338 A | 4/1997 | Fox, Jr. et al. | |
| 5,638,812 A | 6/1997 | Turner | |
| 5,698,229 A | 12/1997 | Ohsumi et al. | |
| 5,712,229 A | 1/1998 | Hopkins et al. | |
| 5,716,406 A | 2/1998 | Farber | |
| 5,763,412 A | 6/1998 | Khan et al. | |
| 5,773,487 A | 6/1998 | Sokol | |
| 5,861,440 A | 1/1999 | Gohla et al. | |
| 6,051,609 A | 4/2000 | Yu et al. | |
| 6,120,784 A | 9/2000 | Snyder, Jr. | |
| 6,127,320 A | 10/2000 | van Ooij et al. | |
| 6,242,526 B1 | 6/2001 | Siddiqui et al. | |
| 6,248,811 B1 | 6/2001 | Ottersbach et al. | |
| 6,326,417 B1 | 12/2001 | Jia | |
| 6,337,357 B1 | 1/2002 | Fukunishi et al. | |
| 6,353,041 B1 | 3/2002 | Qian | |
| 6,413,539 B1 | 7/2002 | Shalaby | |
| 6,475,434 B1 | 11/2002 | Darouiche | |
| 6,488,942 B1 | 12/2002 | Ingemann | |
| 6,492,445 B2 | 12/2002 | Siddiqui et al. | |
| 6,576,633 B1 | 6/2003 | Young et al. | |
| 6,579,539 B2 | 6/2003 | Lawson et al. | |
| 6,719,991 B2 | 4/2004 | Darouiche et al. | |
| 6,723,350 B2 | 4/2004 | Burrell et al. | |
| 6,843,784 B2 | 1/2005 | Modak et al. | |
| 6,846,846 B2 | 1/2005 | Modak et al. | |
| 6,861,060 B1 | 3/2005 | Luriya et al. | |
| 6,887,270 B2 | 5/2005 | Miller et al. | |
| 6,896,889 B2 | 5/2005 | Chevalier et al. | |
| 7,074,839 B2 | 7/2006 | Fansler et al. | |
| 7,098,256 B2 | 8/2006 | Ong et al. | |
| 7,179,849 B2 | 2/2007 | Terry | |
| 7,198,800 B1 | 4/2007 | Ko | |
| 7,232,540 B2 | 6/2007 | Gould et al. | |
| 7,261,925 B2 | 8/2007 | Nesbitt | |
| 7,268,165 B2 | 9/2007 | Greten et al. | |
| 7,407,707 B2 | 8/2008 | Gould et al. | |
| 7,462,401 B2 | 12/2008 | Halfyard et al. | |
| 7,494,339 B2 | 2/2009 | Dias et al. | |
| 7,498,367 B2 | 3/2009 | Qian | |
| 7,514,477 B2 | 4/2009 | Klare et al. | |
| 7,816,434 B2 | 10/2010 | Hackbarth et al. | |
| 8,034,455 B2 | 10/2011 | Wang et al. | |
| 8,227,050 B1 | 7/2012 | O'Neil | |
| 8,263,102 B2 | 9/2012 | Labrecque et al. | |
| 8,388,583 B2 | 3/2013 | Stout et al. | |
| 8,414,547 B2 * | 4/2013 | Difiore et al. | 604/265 |
| 2001/0010016 A1 | 7/2001 | Modak et al. | |
| 2001/0016589 A1 | 8/2001 | Modak et al. | |
| 2001/0056133 A1 | 12/2001 | Montgomery et al. | |
| 2002/0009436 A1 | 1/2002 | Doyle et al. | |
| 2002/0028751 A1 | 3/2002 | Lokkesmoe et al. | |
| 2002/0037260 A1 | 3/2002 | Budny et al. | |
| 2002/0040092 A1 | 4/2002 | Siddiqui et al. | |
| 2002/0064858 A1 | 5/2002 | Yacoby-Zeevi | |
| 2002/0091424 A1 | 7/2002 | Biel | |
| 2002/0119111 A1 | 8/2002 | Kilgour et al. | |
| 2002/0133124 A1 | 9/2002 | Leinsing et al. | |
| 2002/0144705 A1 | 10/2002 | Brattesani et al. | |
| 2003/0072781 A1 | 4/2003 | Pelerin | |
| 2003/0105143 A1 | 6/2003 | Ammendola et al. | |
| 2003/0119932 A1 | 6/2003 | Al-Akhdar et al. | |
| 2003/0134783 A1 | 7/2003 | Harshey et al. | |
| 2003/0147932 A1 | 8/2003 | Nun et al. | |
| 2003/0162839 A1 | 8/2003 | Symington et al. | |
| 2003/0170308 A1 | 9/2003 | Cleary et al. | |
| 2003/0176848 A1 | 9/2003 | Gibson et al. | |
| 2003/0206875 A1 | 11/2003 | Budny et al. | |
| 2003/0215433 A1 | 11/2003 | Kokai-Kun et al. | |
| 2003/0224032 A1 | 12/2003 | Read et al. | |
| 2004/0039349 A1 | 2/2004 | Modak et al. | |
| 2004/0058829 A1 | 3/2004 | Hei et al. | |
| 2004/0109852 A1 | 6/2004 | Xu | |
| 2004/0115477 A1 | 6/2004 | Nesbitt | |
| 2004/0132164 A1 | 7/2004 | Doyle et al. | |
| 2004/0180829 A1 | 9/2004 | Bassler et al. | |
| 2004/0185296 A1 | 9/2004 | Mazzanti | |
| 2004/0230162 A1 | 11/2004 | Tan | |
| 2004/0234475 A1 | 11/2004 | Lannibois-Drean et al. | |
| 2005/0008671 A1 | 1/2005 | Van Antwerp | |
| 2005/0048005 A1 | 3/2005 | Stockel | |
| 2005/0048124 A1 | 3/2005 | Sarangapani | |
| 2005/0059731 A1 | 3/2005 | Albrecht et al. | |
| 2005/0100580 A1 | 5/2005 | Osborne et al. | |
| 2005/0118239 A1 | 6/2005 | Sabesan | |
| 2005/0131356 A1 | 6/2005 | Ash et al. | |
| 2005/0143286 A1 | 6/2005 | Singh et al. | |
| 2005/0158253 A1 | 7/2005 | Budny et al. | |
| 2005/0176905 A1 | 8/2005 | Moon et al. | |
| 2005/0233950 A1 | 10/2005 | Madhyastha | |
| 2005/0265931 A1 | 12/2005 | Qian | |
| 2006/0024372 A1 * | 2/2006 | Utterberg et al. | 424/488 |
| 2006/0165751 A1 | 7/2006 | Chudzik et al. | |
| 2006/0165903 A1 | 7/2006 | Mazzanti | |
| 2006/0239954 A1 | 10/2006 | Sancho | |
| 2006/0258780 A1 | 11/2006 | Chaussade et al. | |
| 2007/0000407 A1 | 1/2007 | Leong | |
| 2007/0112112 A1 | 5/2007 | Kerschner et al. | |
| 2007/0112146 A1 | 5/2007 | Falk et al. | |
| 2007/0141524 A1 | 6/2007 | Brennan et al. | |
| 2007/0160547 A1 | 7/2007 | Duffy et al. | |
| 2007/0166344 A1 | 7/2007 | Qu et al. | |
| 2007/0202177 A1 | 8/2007 | Hoang | |
| 2007/0203574 A1 | 8/2007 | McGrath et al. | |
| 2007/0225179 A1 | 9/2007 | Schutz et al. | |
| 2007/0275101 A1 | 11/2007 | Lu et al. | |
| 2008/0026026 A1 | 1/2008 | Lu et al. | |
| 2008/0051737 A1 * | 2/2008 | Paul et al. | 604/265 |
| 2008/0075761 A1 | 3/2008 | Modak et al. | |
| 2008/0161763 A1 | 7/2008 | Harding et al. | |
| 2008/0182921 A1 | 7/2008 | Suh et al. | |
| 2009/0012220 A1 | 1/2009 | Yamane et al. | |
| 2009/0101152 A1 * | 4/2009 | Burk et al. | 128/207.15 |
| 2009/0110844 A1 | 4/2009 | Platzer et al. | |
| 2009/0114327 A1 | 5/2009 | Breunig | |
| 2009/0162530 A1 | 6/2009 | Nesbitt | |
| 2009/0176907 A1 | 7/2009 | Subramanian et al. | |
| 2009/0188559 A1 | 7/2009 | Nesbitt | |
| 2009/0220739 A1 | 9/2009 | Chougule | |
| 2010/0135949 A1 | 6/2010 | Ou-Yang | |
| 2010/0136209 A1 | 6/2010 | Ou-Yang et al. | |
| 2010/0137379 A1 | 6/2010 | Ou-Yang | |
| 2010/0137472 A1 | 6/2010 | Ou-Yang | |
| 2011/0009831 A1 | 1/2011 | Burkholz et al. | |
| 2011/0065798 A1 | 3/2011 | Hoang et al. | |
| 2011/0301553 A1 | 12/2011 | Goral et al. | |

FOREIGN PATENT DOCUMENTS

| | | |
|---|---|---|
| DE | 4011867 A1 | 10/1991 |
| EP | 0 036 294 A2 | 9/1981 |
| EP | 0 338 418 A1 | 4/1989 |
| EP | 0 379 271 A2 | 1/1990 |
| EP | 0 396 431 A1 | 11/1990 |
| JP | 05-277434 | 10/1993 |
| JP | 09-151262 | 6/1997 |
| JP | 2002-282762 | 10/2002 |
| JP | 2003-342402 | 12/2003 |
| KR | 20020066429 A | 8/2002 |
| WO | WO 98/58690 | 12/1998 |

(56) References Cited

FOREIGN PATENT DOCUMENTS

| WO | WO 98/58989 | 12/1998 |
|----|----|----|
| WO | WO 99/32168 | 7/1999 |
| WO | WO 00/66189 | 11/2000 |
| WO | 2006/056482 A1 | 6/2006 |
| WO | WO 2006/074666 A2 | 7/2006 |
| WO | 2006/099358 A2 | 9/2006 |
| WO | 2007/064835 A2 | 6/2007 |
| WO | WO 2007/100653 A2 | 9/2007 |
| WO | WO 2007/100776 A2 | 9/2007 |
| WO | WO 2008/014447 A2 | 1/2008 |
| WO | 2008/031601 A1 | 3/2008 |
| WO | WO 2008/132045 A2 | 11/2008 |

OTHER PUBLICATIONS

Sage Products, Inc., Preoperative Skin Preparation for the Surgical Patient, http://www.sageproducts.com/products/skin-prep.cfm, 1 page, Oct. 31, 2008.

Sage Products, Inc., Address Multi-Drug Resistant Organisms on the Skin with Early Preop Prep, http://www.sageproducts.com/products/ssi-prevention.cfm, 1 page, Oct. 31, 2008.

Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.

Enturia, ChloraPrep, http://www.enturia.com/products/chloraPrep/chloraPrep-product.html, pp. 1-3, Oct. 31, 2008.

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the internet on Apr. 26, 2011.

McDonnell, G., Russell, A.D. Antiseptics and Disinfectants: Activity, Action, and Resistance. Clinical Microbiology Reviews, (1999) 12(1), pp. 149-179.

* cited by examiner

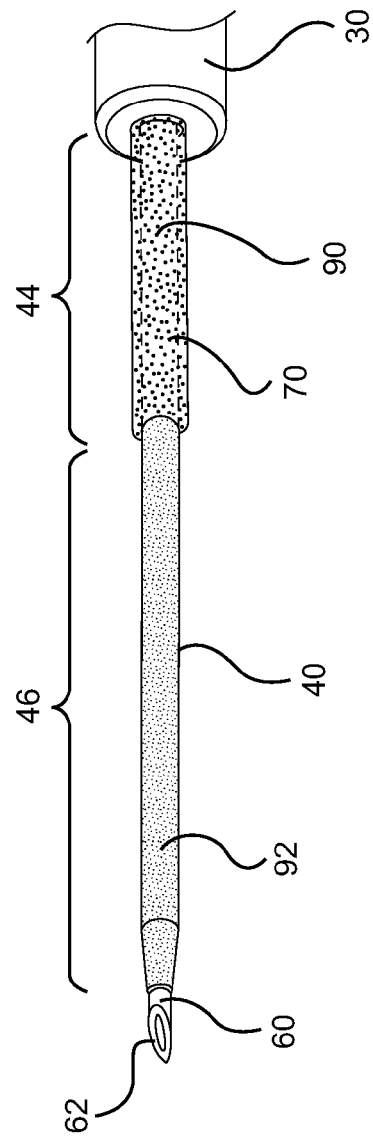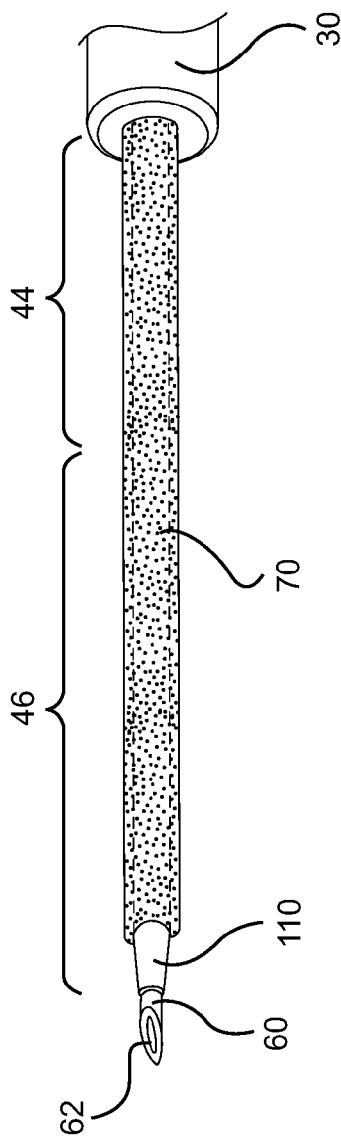
FIG. 8
FIG. 9

ANTIMICROBIAL COATING FOR DERMALLY INVASIVE DEVICES

RELATED APPLICATIONS

This application claims priority to U.S. Provisional Patent Application Ser. No. 61/224,168, filed Jul. 9, 2009 and entitled "ANTIMICROBIAL COATING FOR DERMALLY INVASIVE DEVICES," said application being incorporated herein in its entirety.

BACKGROUND OF THE INVENTION

The current invention relates to a coating for dermally invasive devices. In particular, the present invention relates to methods and systems whereby an antimicrobial coating is applied to the outer surface of a catheter device to prevent infection.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheters are commonly introduced into the vasculature of a patient as part of an intravenous catheter assembly. The catheter assembly generally includes a catheter hub, which supports the catheter, the catheter hub being coupled to a needle hub which supports an introducer needle. The introducer needle is extended and positioned within the catheter such that a beveled portion of the needle is exposed beyond a tip of the catheter. The beveled portion of the needle is used to pierce the skin of the patient to provide an opening whereby to insert the needle in the vasculature of the patient. Following insertion and placement of the catheter, the introducer needle is removed from the catheter thereby providing intravenous access to the patient.

Catheter-related bloodstream infections are caused by the colonization of microorganisms in patients with intravascular catheters and I.V. access devices. These infections are an important cause of illness and excess medical costs, as approximately 250,000 catheter-related bloodstream infections occur in United States intensive care units each year. In addition to the monetary costs, these infections are associated with anywhere from 20,000 to 100,000 deaths each year.

Despite guidelines to help reduce healthcare associated infections (HAIs), catheter-related bloodstream infections continue to plague our healthcare system. The 10 most common pathogens (accounting for 84% of any HAIs) were coagulase-negative staphylococci (15%), *Staphylococcus aureus* (15%), *Enterococcus* species 12%), *Candida* species (11%), *Escherichia coli* (10%), *Pseudomonas aeruginosa* (8%), *Klebsiella pneumoniae* (6%), *Enterobacter* species (5%), *Acinetobacter baumannii* (3%), and *Klebsiella oxytoca* (2%). The pooled mean proportion of pathogenic isolates resistant to antimicrobial agents varied significantly across types of HAI for some pathogen-antimicrobial combinations. As many as 16% of all HAIs were associated with the following multidrug-resistant pathogens: methicillin-resistant *S. aureus* (8% of HAIs), vancomycin-resistant *Enterococcus faecium* (4%), carbapenem-resistant *P. aeruginosa* (2%), extended-spectrum cephalosporin-resistant *K. pneumoniae* (1%), extended-spectrumcephalosporin-resistant *E. coli* (0.5%), and carbanpenem-resistant *A. baumannii, K. pneumoniae, K. oxytoca,* and *E. coli* (0.5%) antimicrobial-resistant pathogens.

Impregnating catheters with various antimicrobial agents is one approach that has been implemented to prevent these infections. These catheters, however, have given less than satisfactory results. In addition, some microbes have developed resistance to the various antimicrobial agents in the system.

Accordingly, there is a need in the art for dermally invasive devices having improved antimicrobial capabilities. Such method and systems are disclosed herein.

BRIEF SUMMARY OF THE INVENTION

In order to overcome the limitations discussed above, the present invention relates to an antimicrobial coating matrix applied to a catheter device such that upon fully inserting the catheter device into a patient, the antimicrobial coating is interposed between the catheter and the dermal layers of the patient.

In some implementations, an antimicrobial formulation is provided as an insoluble coating material that is applied to a transdermal region, surface or portion of a catheter device. The coating material is applied so as to prevent exposure of the coating to the vasculature of the patient. Thus, the patient's bloodstream is preserved from being exposed to any toxicity associated with the antimicrobial formulation.

In some implementations, an antimicrobial formulation is provided as a gel coating. Upon insertion of the catheter, the insertion site acts as a squeegee to remove excess gel coating from the catheter device. The excess coating material remains external to the insertion site thereby forming a pool of antimicrobial agent proximate to the insertion site. In some implementations, trace amounts of antimicrobial agent remain associated with the transdermal portion of the catheter device such that some of the antimicrobial agent is transferred into the insertion site. In other implementations, trace amounts of antimicrobial agent remain associated with the entire outer surface of the catheter, such that a quantity of the antimicrobial agent is exposed to the bloodstream of the patient.

In some implementations, an antimicrobial formulation is provided as a moldable coating material. Upon insertion of the catheter, the insertion site acts as a squeegee to remove excess moldable coating material from the catheter device. The excess coating material remains external to the insertion site where it is manually molded around the catheter and catheter insertion site to form a physical barrier. In some implementations, the intravascular surface of the catheter is further modified to include an anti-thrombogenic coating or lubricant as may be desired to increase the likelihood of blood clots.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 8 is a perspective side view of a catheter device coated with an antimicrobial gel coating and an anti-thrombogenic lube in accordance with a representative embodiment of the present invention.

FIG. 9 is perspective side view of a catheter device coated with an antimicrobial gel coating corresponding to transdermal and intravascular surfaces of the catheter device in accordance with a representative embodiment of the present invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
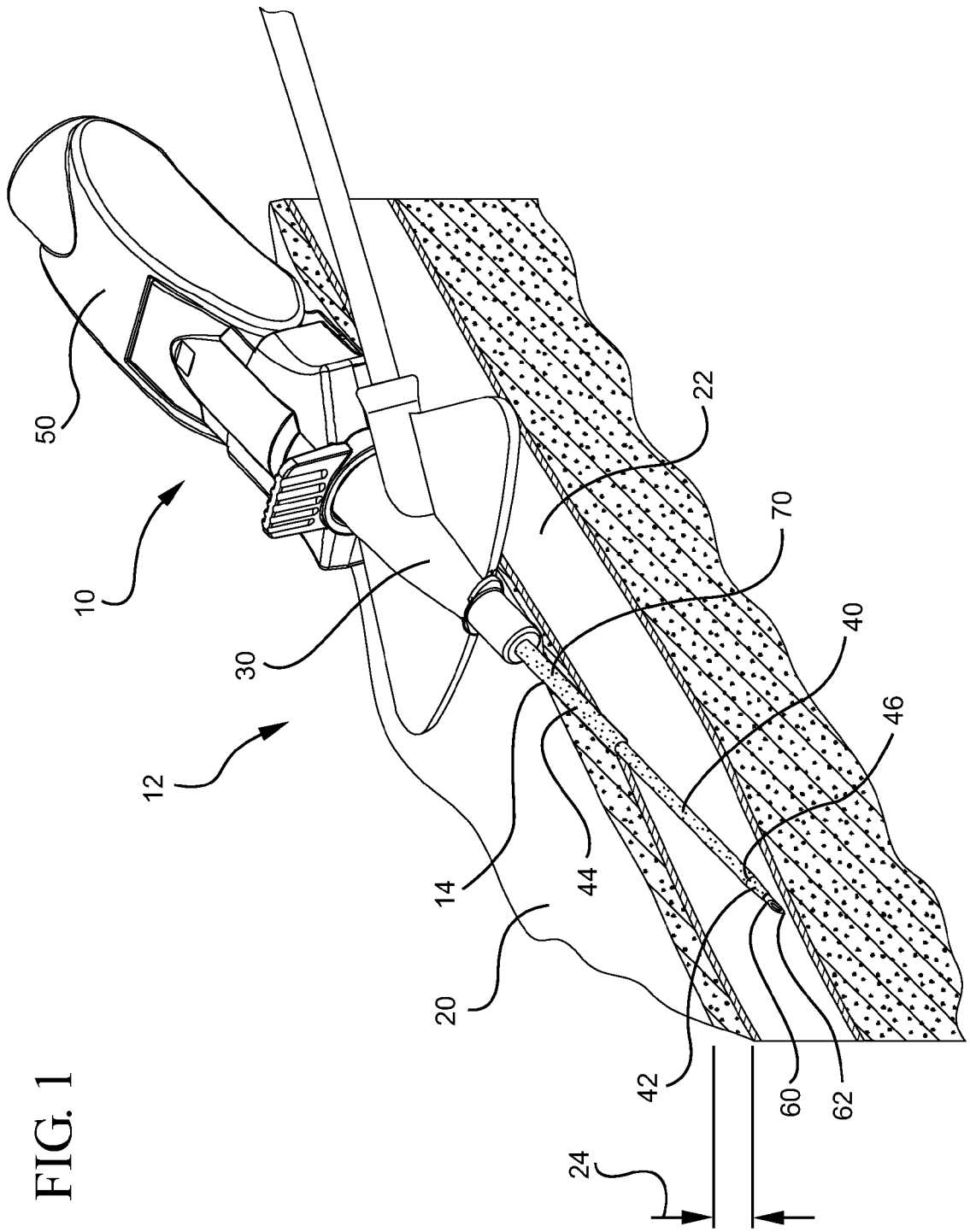
FIG. 1 is a perspective view of a catheter device coated with an antimicrobial coating in accordance with a representative embodiment of the present invention.

Referring now to FIG. 1, a catheter device assembly system 10 is shown. In general, a catheter device system 10 in accordance with the present invention provides access to the vasculature 22 of a patient 20. In some embodiments, catheter device system 10 comprises a catheter hub 30 which supports a catheter tube 40. Catheter tube 40 extends outwardly from catheter hub 30 and is in fluid communication therewith.

In some embodiments, catheter device system 10 further comprises a needle hub 50 which supports an introducer needle 60. Introducer needle 60 is threadedly positioned through catheter hub 30 and catheter tube 40 such that a beveled tip 62 of needle 60 extends beyond catheter tip 42. Beveled tip 62 provides a cutting surface whereby to penetrate the patient's skin 20 and provide access to the patient's vasculature 22. Once catheter 40 is fully inserted into vasculature 22, introducer needle 60 and needle hub 50 are removed thereby providing intravenous access to the patient 20 via catheter 40 and catheter adapter 30.

The inserted catheter 40 is characterized as having a transdermal region or surface 42 and an intravascular region or surface 44. Transdermal surface 44 refers to that portion of catheter 40 that transverses the dermal layer or layers 24 of the patient 20 when catheter 40 is fully inserted into the vasculature 22 of the patient 20. In some embodiments, transdermal surface 44 refers to any portion of catheter 40 that is internally positioned within the patient 20, yet not inserted within vasculature 22. Further, in some embodiments transdermal surface 44 refers to any portion of catheter 40 that is not inserted within vasculature 22 of patient 20. Intravascular surface 46 refers to that portion of catheter 40 that resides within vasculature 22 following complete insertion of catheter 40. Thus, the lengths of the respective surfaces 44 and 46 may vary depending upon the type of catheter device system 10 and the anticipated use.

For example, where a catheter is used to access the peripheral vasculature of a patient, transdermal surface 44 may range from approximately 1 mm to approximately 6 mm in length. However, where a catheter is used to access a non-peripheral vasculature of a patient, transdermal surface 44 may range from approximately 6 mm to approximately 700 mm. For example, such a catheter may include a central vascular catheter system.

In some embodiments, an antimicrobial coating 70 is applied to transdermal surface 44 prior to insertion of catheter 40. Coating 70 is applied to catheter 40 such that after placement of the catheter 40 within the patient 20, coating 70 extends from the point of entrance of the skin 20 to the entrance of the vein 22 and is proximate to the dermal layers 24 of the skin 20. Thus, coating 70 provides a protective barrier between catheter 40 and dermal layers 24. Coating 70 further provides a protective barrier between exterior environment 12 and vasculature 22, thereby preventing or minimizing the possibility of bacterial infection via insertion site 14.

Figure 2:
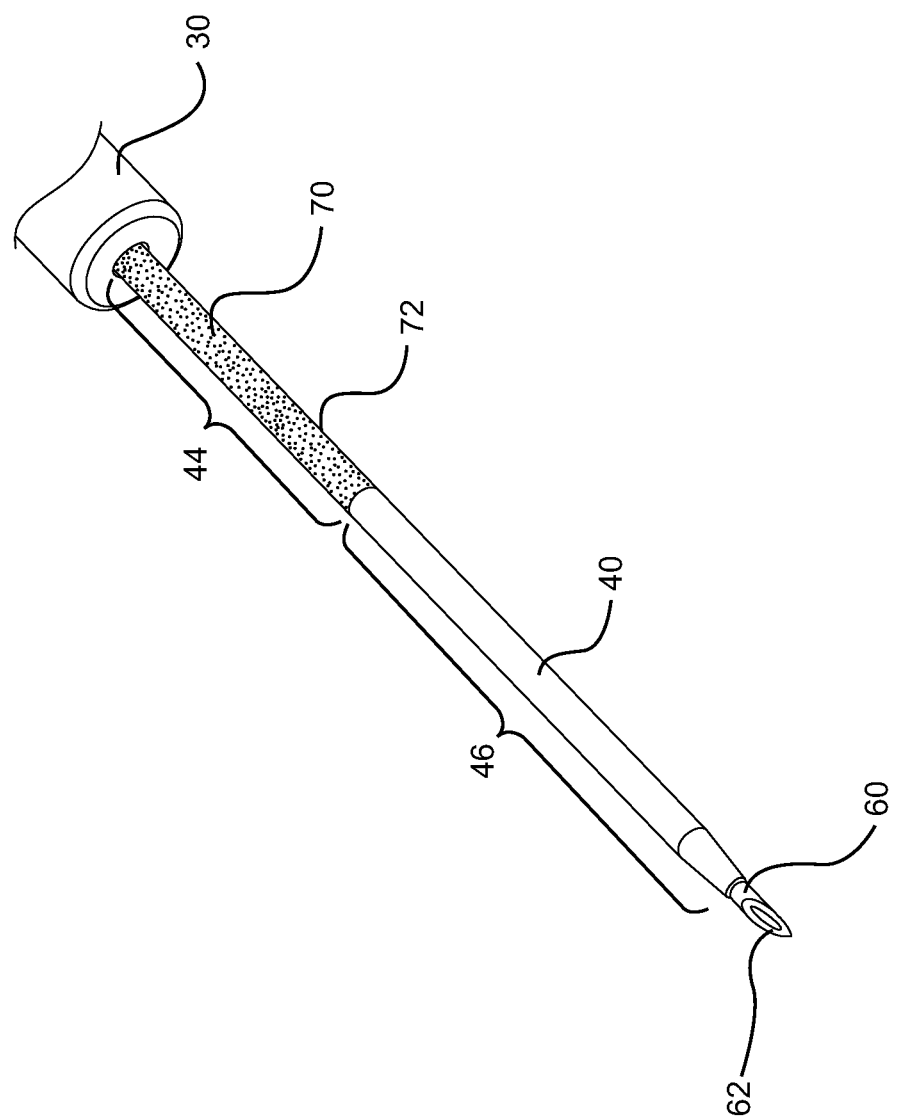
FIG. 2 is a perspective view of a catheter device coated with an antimicrobial coating in accordance with a representative embodiment of the present invention.
Figure 3:
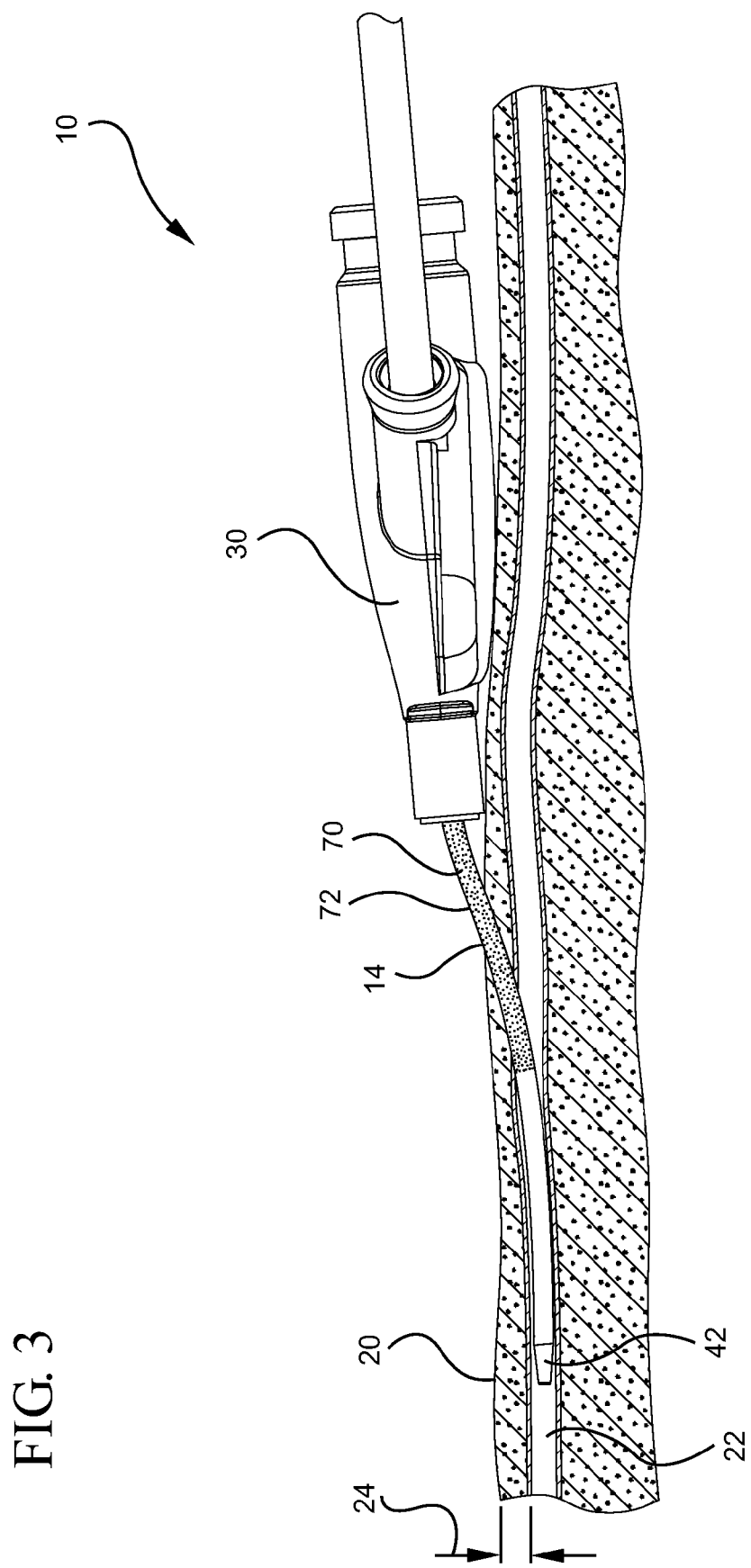
FIG. 3 is a perspective side view of a catheter device coated with an antimicrobial coating and inserted into a patient in accordance with a representative embodiment of the present invention.

In some embodiments, coating 70 comprises a thin soluble or insoluble polymer matrix 72 disposed on transdermal portion 44, as shown in FIG. 2. As previously discussed, the location of matrix 72 is such that after placement of the device 10, transdermal portion 44 extends from the point of entrance 14 to the entrance of the vein 22, as shown in FIG. 3.

Figure 4A:
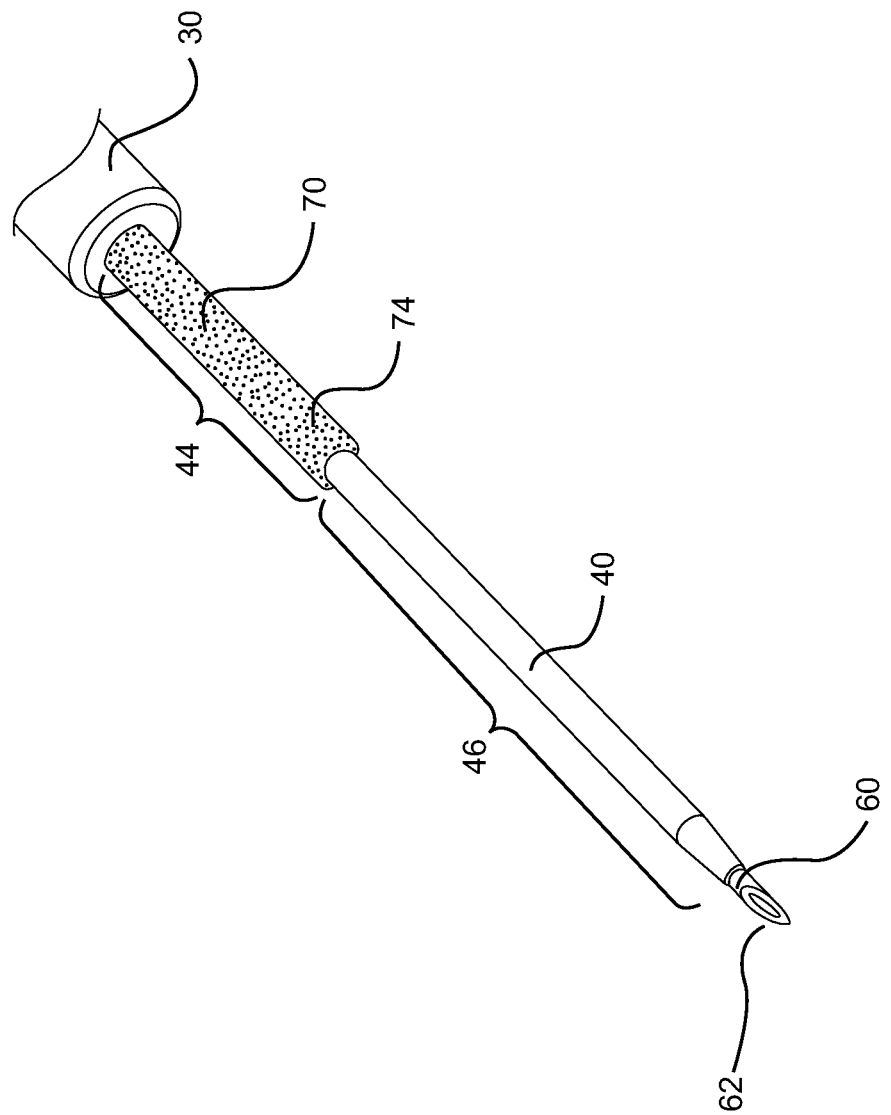
FIG. 4A is a perspective view of a catheter device coated with an antimicrobial gel coating in accordance with a representative embodiment of the present invention.
Figure 4B:
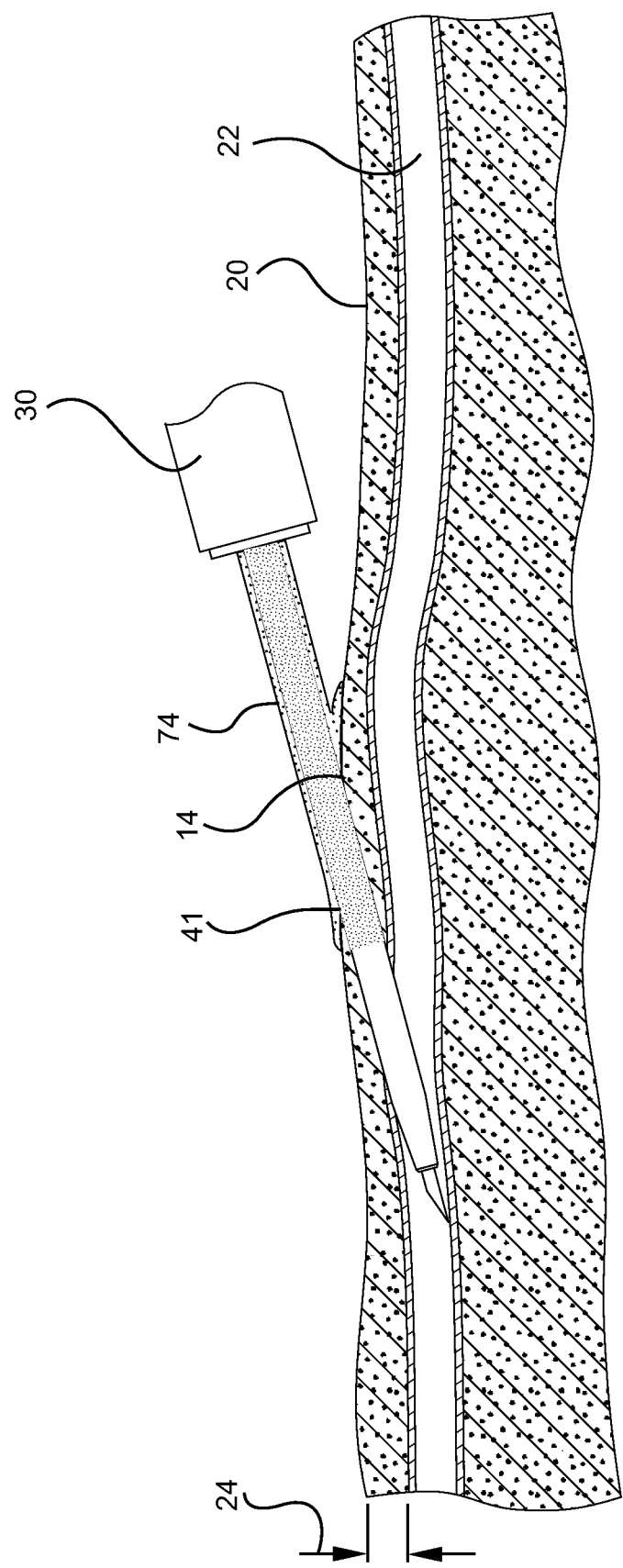
FIG. 4B is a perspective view of a catheter device coated with an antimicrobial gel coating during insertion of the catheter into a patient in accordance with a representative embodiment of the present invention.
Figure 5:
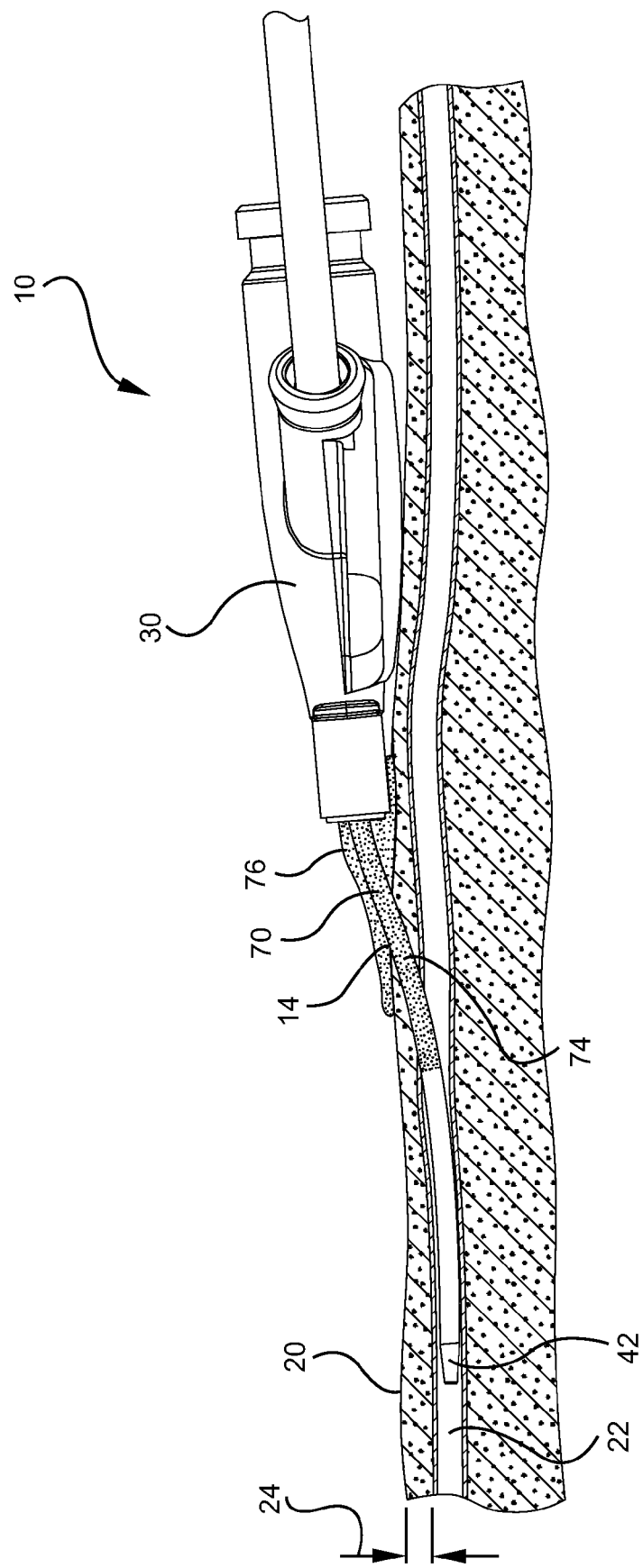
FIG. 5 is a perspective side view of a catheter device coated with an antimicrobial gel coating and inserted into a patient in accordance with a representative embodiment of the present invention.

In some embodiments, coating 70 comprises a viscous and lubricious gel matrix 74 disposed on transdermal surface 44, as shown in FIG. 4A. Upon insertion of catheter 40 into patient 20, insertion site 14 acts as a squeegee to remove excess matrix 74 from transdermal surface 44, as shown in FIG. 4B. Excess matrix 74 remains external to patient 20 thereby forming a pool 76 of matrix 74 proximate to and surrounding insertion site 14, as shown in FIG. 5.

Pool 76 provides a physical barrier of antimicrobial coating material 70 thereby further preventing introduction of unwanted microorganisms into insertion site 14. In some embodiments, trace amounts of matrix 74 remain associated with transdermal surface 44 through dermal layers 24. Thus, matrix 74 provides both external and internal protection relative to insertion site 14. In some embodiments, the squeegee function of insertion site 14 removes matrix 74 to provide a gradient of coating 70 over transdermal surface 44. In other embodiments a combination of the squeegee function of insertion site 14 and a solubility of matrix 74 provides a gradient of coating 70 over transdermal surface 44.

Figure 6:
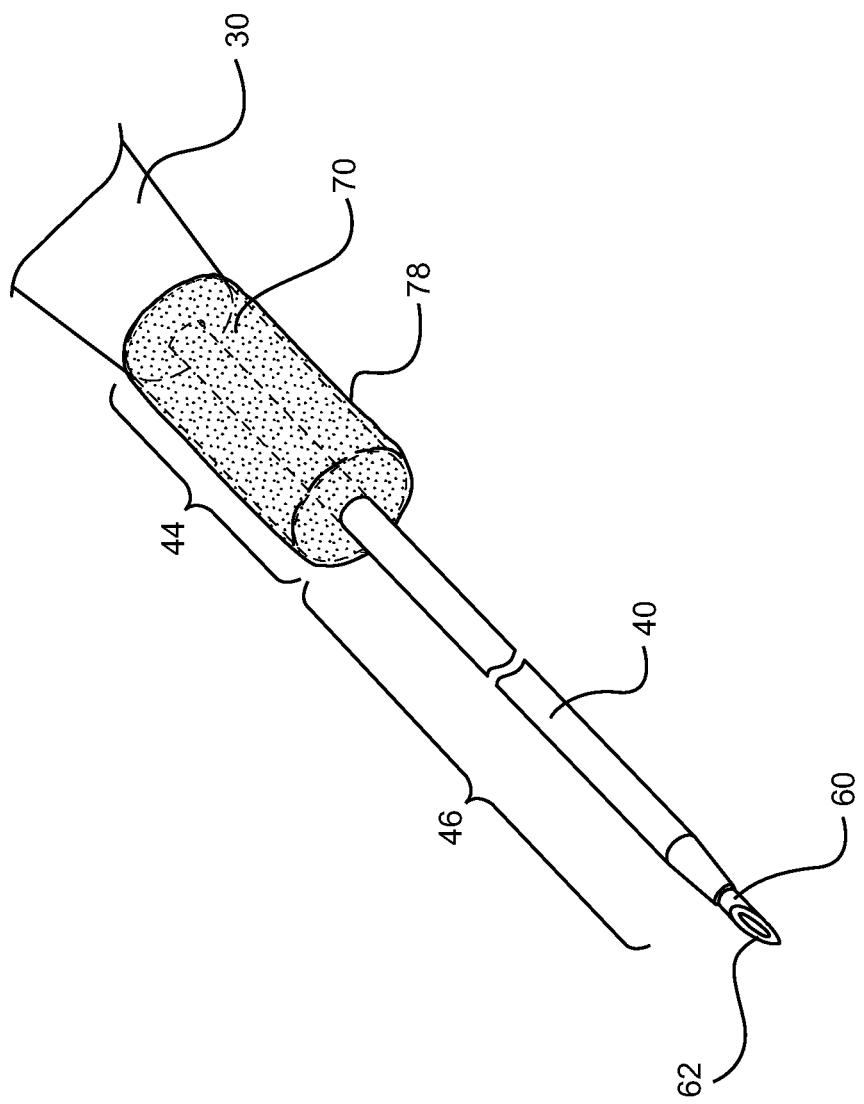
FIG. 6 is a perspective view of a catheter device coated with a moldable antimicrobial coating in accordance with a representative embodiment of the present invention.
Figure 7:
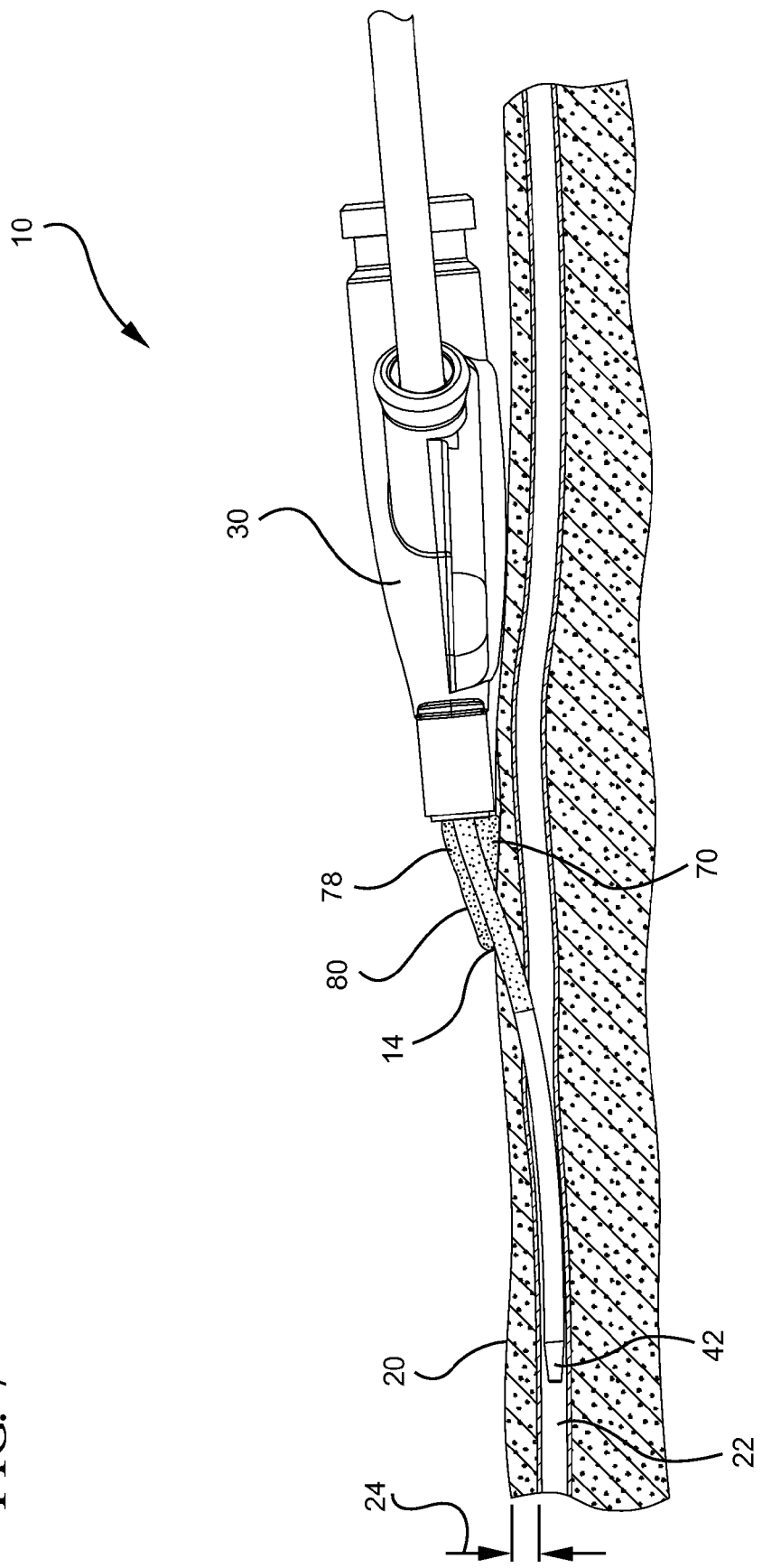
FIG. 7 is a perspective side view of a catheter device coated with a moldable antimicrobial coating and inserted into a patient in accordance with a representative embodiment of the present invention.

In some embodiments, coating 70 comprises a conformable, putty-like matrix 78 disposed on transdermal surface 44, as shown in FIG. 6. Upon insertion of catheter 40 into patient 20, insertion site 14 acts as a squeegee to remove excess matrix 78 from transdermal surface 44. Excess matrix 78 remains external to patient 20 as a moldable mass 80, as shown in FIG. 7. Moldable mass 80 is then capable of being manually molded to cover insertion site 14 and any area proximate thereto, as may be desired. In some embodiments, trace amounts of matrix 78 remain associated with transdermal surface 44 through dermal layers 24. Thus, matrix 78 provides both external and internal protection relative to insertion site 14.

Referring now to FIG. 8, in some embodiments coating 70 further comprises a biocompatible dye substance 90 that provides a color indication of continued antimicrobial activity. For example, in some embodiments dye substance 90 provides a first color in the absence of microbial activity, and provides a second color in the presence of microbial activity. In general, dye substance 90 is positioned on catheter 40 so as to be proximate to insertion site 14. Thus, any microbial activity proximate to insertion site 14 will be indicated by dye 90.

In some embodiments, catheter 40 further comprises an anti-thrombogenic lube 92 corresponding to intravascular surface 46. Anti-thrombogenic lube 92 decreases the likelihood of blood clotting for the intravascular portion 46 of catheter 40. Accordingly, in some embodiments the anti-thrombogenic lube 92 is at least partially soluble to aid the mobility and effectiveness of the anti-thrombogenic properties. By restricting the placement of coating 70 and lube 92 to those portions of the catheter which will be in contact with the targeted tissues, i.e.: dermal layers 24 and vasculature 22, respectively, toxicity from coating 70 is minimized while limiting clot potential.

Figure 10:
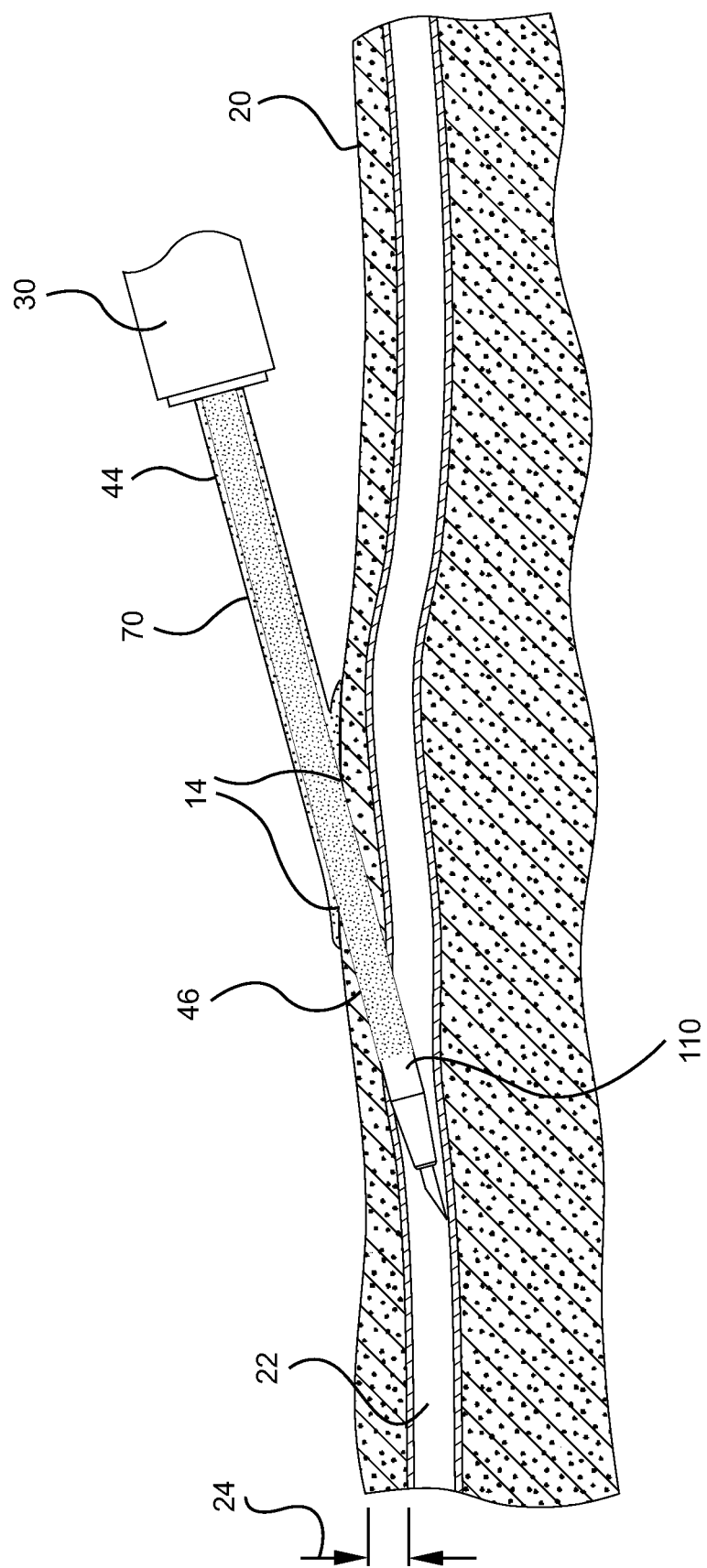
FIG. 10 is a perspective view of a catheter device coated with an antimicrobial gel coating during insertion of the catheter into a patient in accordance with a representative embodiment of the present invention.

With reference to FIG. 9, in some embodiments coating 70 is disposed over both the transdermal 44 and intravascular 46 surfaces of catheter 110. Upon insertion of catheter 110, insertion site 14 acts as a squeegee to remove excess coating 70, as discussed above and shown in FIG. 10. In some embodiments, residual amounts of coating 70 remain associated with intravascular 46 and transdermal 44 surface of catheter 110, thereby providing antimicrobial protection over the entire length of catheter 110. In some embodiments, coating 70 is at least partially soluble to aid the mobility and effectiveness of the coating. For example, where coating 70 is at least partially soluble, coating 70 is readily mobilized when brought into contact with a bodily fluid of patient 20. In some embodiments, coating 70 is disposed over the length of catheter 110 in a decreasing or increasing gradient from catheter hub 30 to catheter tip 42. Further, in some embodiments coating 70 comprises a mixture of an antimicrobial agent, an anti-thrombogenic lube, and a biocompatible dye substance.

Figure 11:
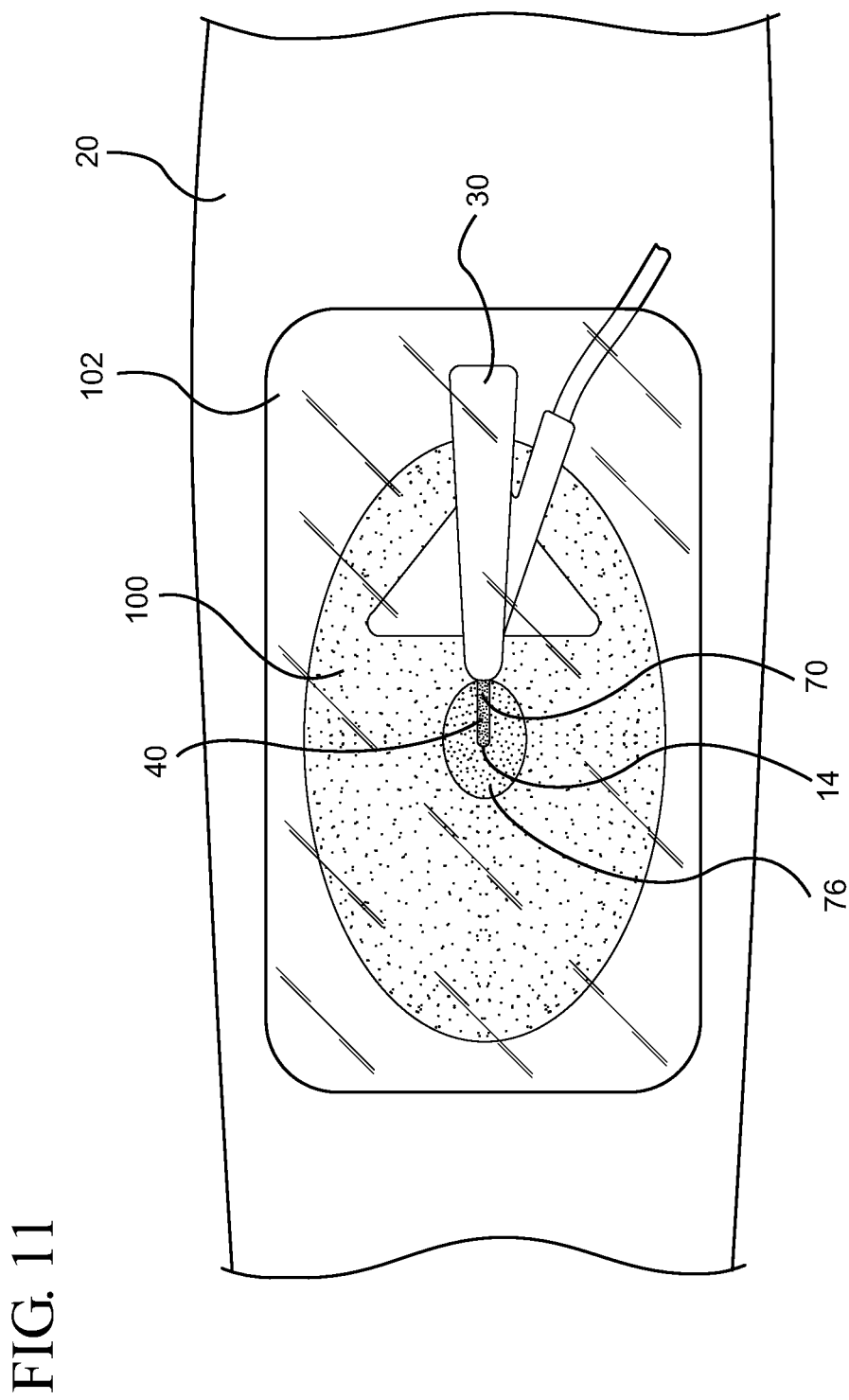
FIG. 11 is a top view of an insertion site and an inserted catheter device further protected with an antimicrobial dressing and skin prep treatment in accordance with a representative embodiment of the present invention.
Figure 12:
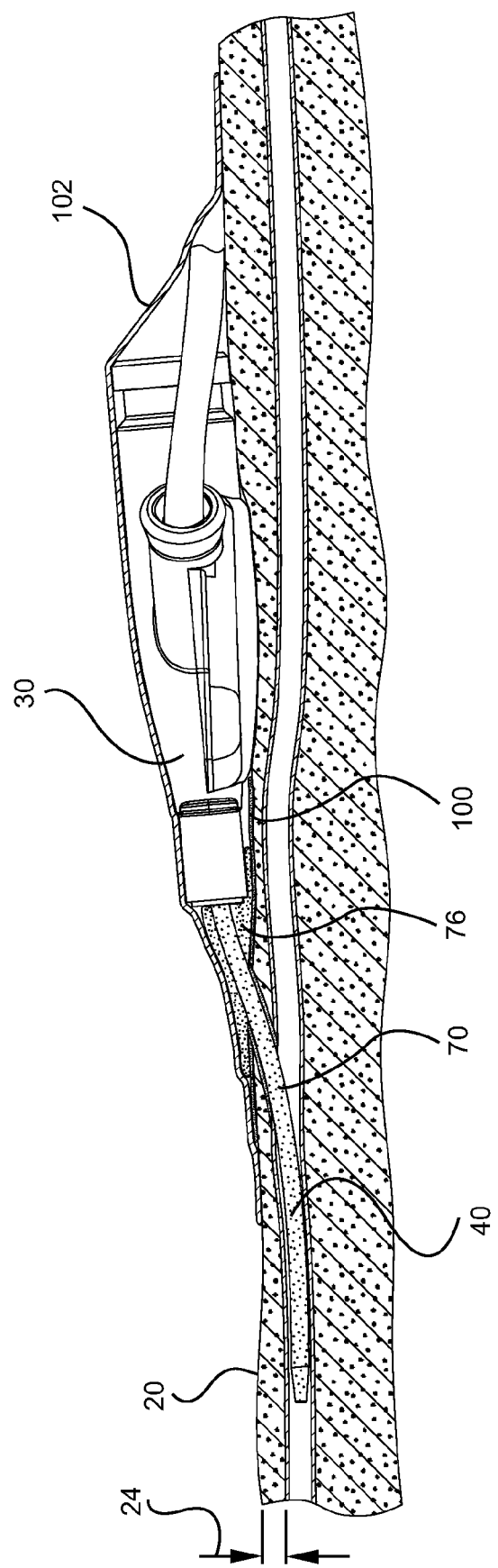
FIG. 12 is a perspective side view of a catheter device coated with an antimicrobial gel coating inserted into a patient, the catheter device further including an antimicrobial dressing and skin prep treatment in accordance with a representative embodiment of the present invention.

In some embodiments, catheter 40 and insertion site 14 are further combined with an antimicrobial insertion site preparation 100 and an antimicrobial dressing 102, as shown in FIGS. 11 and 12. For example, in some embodiments, a potential insertion site 14 of patient 20 is first prepared with an antimicrobial preparation 100, such as an iodine scrub. Catheter 40 and introducer needle 60 are then inserted into insertion site 14. In some embodiments, coating 70 forms a pool 76 which surrounds insertion site 14, as discussed above. Following insertion, introducer needle 60 is removed and antimicrobial dressing 102 is provided as an external barrier for catheter 40 and catheter adapter 30. Thus, in some embodiments additional antimicrobial protection is provided to further protect insertion site 14 from microbial activity.

In general, the present invention relates to a novel antimicrobial formulation that contains antimicrobial agents used to disinfect a catheter and catheter insertion site of a patient. As previously discussed, the antimicrobial formulation may be provided in various consistencies and forms to allow for various coating methods as may be desired. The coating of the antimicrobial agent(s) on the surface of medical devices prevents the growth of unwanted microorganisms, as well as reduces microorganism colonization on the medical devices during normal application, i.e. prevent contamination due to contacting skin flora of the patient, or due to microorganism exposure prior to patient contact. In addition, due to a reduction in the colonization of microorganisms, the medical device may be left in the patient for extended lengths of time without causing infection.

In some embodiments, a coating is provided comprising a mixture of antimicrobial agents which are selected to provide long lasting antimicrobial efficacy after multiple applications. For example, in some embodiments antimicrobial agents are selected and formulated in a polymer matrix having very low solubility in water. Thus, the antimicrobial formulations withstand multiple procedures, such as blood drawings, drug infusion, TPN procedures, as well as saline and heparin flushes.

In some embodiments, antimicrobial coating 70 comprises a matrix of one or more antimicrobial agents. Non-limiting examples of coating 70 are shown in Table 1.

TABLE 1

| Formula | 1 | 2 | 3 | 4 | 5 | 6 | 7 | 8 | 9 | 10 | 11 |
|---|---|---|---|---|---|---|---|---|---|---|---|
| Ethyl alcohol | 70.00 | | 70.00 | 70.00 | | 70.00 | | | 70.00 | 24.0 | 24.0 |
| Isopropyl alcohol | | 70.00 | | | 70.00 | | 70.00 | 70.00 | | | |
| THF | | | | | | | | | | 70 | 70 |
| Chlorhexidine Gluconate | 4.00 | 4.00 | 4.00 | 4.00 | 4.00 | 4.00 | 4.00 | 4.00 | 4.00 | 5.00 | 5.00 |
| Chloroxylenol | | | 0.10 | | 0.10 | | | | | | |
| Triclosan | 0.10 | 0.10 | | 0.10 | | | | | | | |
| Hexetidine | | | | | | 0.10 | 0.10 | | | | |
| PCMX | | | | | | | | | 0.10 | 0.10 | |
| Cationic polymer | | | 1.0 | 0.10 | | | | | | | |
| Chitosan | 1.0 | | | | | | | 1.0 | | | |

TABLE 1-continued

| Formula | 1 | 2 | 3 | 4 | 5 | 6 | 7 | 8 | 9 | 10 | 11 |
|---|---|---|---|---|---|---|---|---|---|---|---|
| Polyurethane | | | | | | | | | | | 1.0 |
| Polyvinyl alcohol | | | | | | | | | | 1.0 | |
| Water | 24.90 | 25.90 | 24.90 | 24.90 | 25.90 | 25.90 | 25.90 | 24.90 | 25.90 | | |

For example, in some embodiments coating 70 comprises an alcohol component. Suitable alcohol components generally include a lower alcohol having between one and six carbons ($C_1$-$C_6$). In some embodiments, coating 70 comprises an alcohol component selected from the group consisting of ethyl alcohol, isopropanol, propanol, and butanol. In other embodiments, coating 70 comprises two or more lower alcohol components, for example a mixture of isopropyl alcohol and ethyl alcohol in a ratio of about 1:10 to about 1:1. Further, in some embodiments coating 70 comprises a mixture of more than two alcohol components.

In some embodiments, coating 70 comprises an alcohol component in an amount approximately equal to 40% (w/v) of coating 70. In other embodiments, coating 70 comprises an alcohol component in an amount from approximately 20% (w/v) to approximately 95% (w/v).

In some embodiments, coating 70 further comprises one or more fugitive solvents, such as tetrahydrofuran (THF), methylethylketone (MEK) and hexane solvents. In some embodiments, coating 70 comprises a fugitive solvent in an amount approximately equal to 70% (w/v) of coating 70. In other embodiments, coating 70 comprises two or more fugitive solvents.

Antimicrobial coating 70 generally comprises an antimicrobial or biocidal agent effective against various forms and strains of bacteria which may cause infection within the patient 20. The terms "biocidal agent" or "biocide," as used herein refer to an agent that destroys, inhibits and/or prevents the propagation, growth, colonization and multiplication of unwanted organisms. The term "organism" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Specific examples of such organisms include the fungi *Aspergillus niger, Aspergillus flavus, Rhizopus nigricans, Cladsprorium herbarium, Epidermophyton floccosum, Trichophyton mentagrophytes, Histoplasma capsulatum*, and the like; bacteria such as *Pseudomanas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like; and yeast such as *Saccharomcyces cerevisiae, Candida albicans*, and the like. Additionally, spores of microorganisms, viruses and the like are organisms within the scope of the present invention.

Biocidal agents suitable for use in the present invention include, but are not limited to, biocides such as phenol, quaternary ammonium, and guanidine containing biocides. For example, in some embodiments coating 70 comprises a biocidal agent selected from taurolidine, parachlorometaxylenol, silver sulfadiazine, silver oxide, and silver nitrate. In other embodiments, coating 70 comprises a biocidal agent selected from a pyridinium biocide, benzalkonium chloride, cetrimide, benethonium chloride, cetylpyridinium chloride, dequalinium acetate, dequalinium chloride, and chloroxylenol.

Further, in some embodiments coating 70 comprises a biocidal agent selected from chlorhexidine base, chlorhexidine gluconate, chlorhexidine acetate, chlorhexidine hydrochloride, chlorhexidine dihydrochloride, dibromopropamidine, halogenated diphenylalkanes, carbanilide, salicylanilide, tetrachlorosalicylanilide, trichlorocarbanilide, and mixtures thereof. Still further, in some embodiments coating 70 comprises a biocidal agent selected from chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride, and combinations thereof.

In some embodiments, coating 70 comprises one or more biocidal agents in an amount from approximately 0.01% (w/v) to approximately 10.0% (w/v) of coating 70. In other embodiments, coating 70 comprises one or more biocidal agents in an amount from approximately 0.01% (w/v) to approximately 5.0% (w/v) of coating 70.

In some embodiments, the longevity of the antimicrobial coating was increased by adding a cationic polymer to the formulation. The cationic polymer combined with the antimicrobial agent, thereby forming a bond with the surface of the medical device. Thus, when the antimicrobial coating was applied to the surface of the medical device, a solvent of the coating was evaporated thereby leaving the antimicrobial agent and cationic polymer bound to the medical device. Non-limiting examples of cationic polymers include cellulosic polymer, chitosan, polyvinyl alcohol, polyvinyl pyrrolidone, polyvinyl acetate, polyurethane, and water-soluble cellulose. In some embodiments, a cationic polymer was selected which was soluble in alcohol, but insoluble in water. In other embodiments, a cationic polymer was selected that was soluble in water.

In some embodiments, antimicrobial coating 70 is prepared with simple mixing of the various ingredients at room temperature. Typically, organic solvents or alcohols, and water components are mixed first, followed by the addition of the other ingredients, in any order. Formulations 1-11, of Table 1, were prepared with ingredients as shown in Table 2.

TABLE 2

| Ingredient | Supplier |
|---|---|
| Ethanol (190 proof) | Grain Processing Inc. |
| Isopropyl Alcohol - (IPA) (>99% alcohol) | J T Baker Phillipsburg, New Jersey |
| Chlorhexidine Gluconate (20%) | Xttrium Laboratories Chicago, Illinois |
| Triclosan | Ciba Specialty Chemicals |
| Chlorhexidine Diacetate | Uhe and Fragchem |
| Chloroxylenol | Clarien North Carolina |
| Ethyl Cellulose | The Dow Chemical Company Midland, Michigan |
| THF or MEK or Hexanes Solvent | Sigma Aldrich, Fisher Scientific |
| USP water | Becton Dickinson |
| Cationic Cellulosic polymer | Amerchol Corporation, A Subsidiary of DOW Chemical Company |

The present invention may be embodied in other specific forms without departing from its structures, methods, or other essential characteristics as broadly described herein and claimed hereinafter. For example, the present invention may be applied to any dermally invasive device, such as needles, scalpels, trocars, endoscopes, stoma appliances, and the like. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An antimicrobial catheter device, comprising:
a catheter having a tip end, a base end, and an extended portion extending therebetween, the catheter further having an outer surface including a transdermal surface and an intravascular surface; and
an antimicrobial agent in the form of a manipulatably adjustable, putty-like matrix applied to the transdermal surface of the outer surface of the catheter, wherein following insertion of the catheter into a patient, a first portion of the antimicrobial agent remains applied to the transdermal surface and is in contact with dermal layers of the patient, and a second portion of the antimicrobial agent is removed from the transdermal surface and deposited external to and surrounding an insertion site into which the catheter is inserted, thereby forming a manually moldable mass of antimicrobial agent proximate to the insertion site.

2. The device of claim 1, wherein the antimicrobial agent comprises:
a polymer component;
a fugitive solvent component;
an alcohol component; and
a biocidal agent.

3. The device of claim 2, wherein the polymer component comprises a cationic polymer component.

4. The device of claim 2, wherein the polymer component is insoluble in water.

5. The device of claim 4, wherein the polymer component is at least one of cellulosic polymer, chitosan, polyvinyl alcohol, polyvinyl pyrrolidone, polyvinyl acetate, polyurethane.

6. The device of claim 2, wherein the polymer component is water soluble.

7. The device of claim 2, wherein the biocidal agent is present in an amount from approximately 0.01% (w/v) to approximately 10.0% (w/v).

8. The device of claim 2, wherein the biocidal agent is present in an amount from approximately 0.01% (w/v) to approximately 5.0% (w/v).

9. The device of claim 2, wherein the polymer component is present in an amount from approximately 0.001% (w/v) to approximately 5.0% (w/v).

10. The device of claim 2, wherein the biocidal agent is at least one of chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride.

11. The device of claim 2, wherein the alcohol component comprises a lower alcohol having between one and six carbon atoms.

12. The device of claim 2, wherein the alcohol component is present within the antimicrobial agent in an amount approximately equal to 20% (w/v).

13. The device of claim 2, wherein the alcohol component comprises a mixture of isopropyl alcohol and ethanol and is present within the antimicrobial agent in an amount from approximately 40% (w/v) to approximately 95% (w/v).

14. The device of claim 2, wherein the fugitive solvent comprises an organic solvent that is present within the antimicrobial agent in an amount from approximately 20% (w/v) to approximately 95% (w/v).

15. The device of claim 2, wherein the polymer component comprises a cationic polymer.

16. The device of claim 1, wherein the antimicrobial agent comprises:
ethanol;
isopropyl alcohol;
chlorhexidine gluconate;
triclosan;
chlorhexidine diacetate;
chloroxylenol;
ethyl cellulose;
tetrahydrofuran, methyl ethyl ketone, or hexane;
water; and
cationic cellulosic polymer.

17. The device of claim 16, wherein the ethanol is present within the antimicrobial agent in an amount of 70% (w/v).

18. The device of claim 16, wherein the chlorhexidine gluconate is present within the antimicrobial agent in an amount of 4% (w/v).

19. The device of claim 16, wherein the chloroxylenol is present within the antimicrobial agent in an amount of 0.1% (w/v).

20. The device of claim 16, wherein the antimicrobial agent comprises a biocompatible bacteria-indicator dye.

21. An antimicrobial catheter device, comprising:
a catheter having a tip end, a base end, and an extended portion extending therebetween, the catheter further having an outer surface including a transdermal surface and an intravascular surface; and
an antimicrobial agent applied to the transdermal surface of the outer surface of the catheter, wherein following insertion of the catheter into a patient, at least a portion of the antimicrobial agent remains applied to the transdermal surface and is in contact with dermal layers of the patient;
wherein the antimicrobial agent comprises:
ethanol;
isopropyl alcohol;
chlorhexidine gluconate;
triclosan;
chlorhexidine diacetate;
chloroxylenol;
ethyl cellulose;
tetrahydrofuran, methyl ethyl ketone, or hexane;
water; and
cationic cellulosic polymer.

* * * * *